(12) United States Patent
Hentschel et al.

(10) Patent No.: US 7,873,518 B2
(45) Date of Patent: Jan. 18, 2011

(54) DEVICE AND METHOD FOR ASSESSING A QUALITY CLASS OF AN OBJECT TO BE TESTED

(75) Inventors: Dieter Hentschel, Dresden (DE); Constanze Tschoepe, Dresden (DE); Ruediger Hoffmann, Dresden (DE); Matthias Eichner, Berlin (DE); Matthias Wolff, Goerlitz (DE)

(73) Assignees: Fraunhofer-Gesellschaft zur Foerderung der angewandten Forschung e.V., Munich (DE); Technische Universitaet Dresden, Dresden (DE)

( * ) Notice: Subject to any disclaimer, the term of this patent is extended or adjusted under 35 U.S.C. 154(b) by 97 days.

(21) Appl. No.: 11/558,816

(22) Filed: Nov. 10, 2006

(65) Prior Publication Data

US 2007/0100623 A1 May 3, 2007

Related U.S. Application Data

(63) Continuation of application No. PCT/EP2005/003573, filed on Apr. 5, 2005.

(30) Foreign Application Priority Data

May 13, 2004 (DE) .................. 10 2004 023 824

(51) Int. Cl.
*G10L 15/14* (2006.01)
(52) U.S. Cl. .................................. 704/256.1
(58) Field of Classification Search ....... 704/256–256.5
See application file for complete search history.

(56) References Cited

U.S. PATENT DOCUMENTS

| 5,465,321 | A | | 11/1995 | Smyth et al. .................. 395/22 |
| 5,500,941 | A | * | 3/1996 | Gil .............................. 714/38 |
| 5,539,652 | A | * | 7/1996 | Tegethoff ..................... 703/14 |
| 5,778,341 | A | * | 7/1998 | Zeljkovic ..................... 704/256 |
| 5,867,813 | A | * | 2/1999 | Di Pietro et al. ............ 704/202 |
| 5,924,066 | A | * | 7/1999 | Kundu ......................... 704/232 |
| 5,970,452 | A | * | 10/1999 | Aktas et al. ................. 704/253 |

(Continued)

OTHER PUBLICATIONS

F. Wolfertstetter and G. Ruske; Discriminative Training of Stochastic Markov Graphs for Speech Recognition; Acoustic, Speech, and Signal Processing conference Pr International conference on 1996, ICASSP-96, vol. 2, May 7-10, 1996, pp. 581-584.*

(Continued)

*Primary Examiner*—Jakieda R Jackson
(74) *Attorney, Agent, or Firm*—Glenn Patent Group; Michael A. Glenn

(57) ABSTRACT

A device for assessing a quality class of an object to be tested includes a unit for detecting a test signal from the object to be tested. Furthermore, the device for assessing includes a unit for providing a stochastic Markov model including states and transitions between states on the basis of reference measurements of objects of known quality classes, and a unit for evaluating the test signal using the stochastic Markov model. In addition, the device for assessing includes a unit for associating the object to be tested with a quality class based on the evaluation of the test signal. Such a device has the advantage to be able to perform a more precise association of an object to be tested with a quality class as compared to prior art.

23 Claims, 5 Drawing Sheets

U.S. PATENT DOCUMENTS

| | | | |
|---|---|---|---|
| 6,366,887 B1* | 4/2002 | Zehner et al. | 704/278 |
| 6,477,485 B1 | 11/2002 | Dragan et al. | 702/187 |
| 6,591,226 B1* | 7/2003 | Hartmann et al. | 702/183 |
| 6,850,888 B1* | 2/2005 | Gao et al. | 704/256 |
| 2001/0047265 A1* | 11/2001 | Sepe, Jr. | 704/275 |
| 2002/0128989 A1* | 9/2002 | Thess et al. | 706/16 |
| 2003/0233233 A1* | 12/2003 | Hong | 704/256 |
| 2005/0049873 A1* | 3/2005 | Bartur et al. | 704/256 |

OTHER PUBLICATIONS

P. Holstein et al., "A Strategy for Signal Recognition under Adverse Conditions," in Proceedings of 32$^{nd}$ International Congress and Exposition on Noise Control Engineering, Jeju International Convention Center, Seogwipo, Korea, Aug. 25-28, 2003, Jeju, Korea.

Z. Daofu, et al., "The Pattern Recognition of Non-Destructive Testing Based on HMM," in Proceedings 4$^{th}$ World Congress on Intelligent Control and Automation (Cat. No. 02EX527), Jun. 10-14, 2002, vol. 3, pp. 2198-2202, Shanghai, P. R. China.

P. Baruah et al., "HMMS for Diagnostics and Prognostics in Machining Processes," in Proceedings 57$^{th}$ Meeting of the Society for Machinery Failure Prevention Technology, 2003, pp. 389-398, Virginia Beach, USA.

A. R. Taylor et al., "A Comparison of Techniques for Monitoring Process Faults," in Proceedings Conference Control Systems, 2002, pp. 323-327, Stockholm, Sweden.

H.Y.K. Lau, "A Hidden Markov Model-Based Assembly Contact Recognition System," Mechatronics, vol. 13 (8-9), pp. 1001-1023, 2003, ISSN 0957-4158.

F. Wolfertstetter et al., "Structured Markov Models for Speech Recognition Using Stochastic Markov Graphs," in Proceedings 6$^{th}$ International Conference Spoken Lanquage Processing (ICSLP), 2000, vol. 1, pp. 701-704, Beijing, PR China.

M. Eichner et al., "Speech Synthesis using Stochastic Markov Graphs," in Proceedings ICASSP, May 5-7, 2001, Salt Lake City, Utah.

D. Whitney et al., "Multi-Scale Signal Feature Processing for Automatic, Objective Vehicle Noise and Vibration Quality Analysis," Acoustics, Speech, and Signal Processing, 1995, ICASSP-95, 1995 International Conference in Detroit, Mi, May 9-12, 1995, New York, NY, IEEE, pp. 2959-2962, XP010151965.

C.Tshope et al., "Classification of Non-Speech Acoustic Signals Using Structure Models," Acoustics, Speech, and Signal Processing, 2004, Proceedings ICASSP '04, IEEE, International Conference in Montreal, Quebec, Canada, May 17-21, 2004, Piscataway, NJ.

M. Eichner et al., "A Unified Approach for Speech Synthesis and Speech Recognition Using Stochastic Markov Graphs," in Proceedings 6$^{th}$ International Conference of Spoken Language Processing (ICSLP), 2000, vol. 1, pp. 701-704, Beijing, P.R. China.

* cited by examiner

DEVICE AND METHOD FOR ASSESSING A QUALITY CLASS OF AN OBJECT TO BE TESTED

CROSS-REFERENCE TO RELATED APPLICATION

This application is a continuation of copending International Application No. PCT/EP2005/003573, filed on Apr. 5, 2005, which designated the United States and was not published in English, which claims priority of German Patent Application 10 2004 023 824.3, filed on May 13, 2004.

BACKGROUND OF THE INVENTION

1. Field of the Invention

The present invention relates to the technical field of non-destructive testing, and the present invention particularly relates to a method and a device for the classification of an object to be tested into a quality class using acoustic signals.

2. Description of the Related Art

In order to be able to determine the wear or the remaining lifetime of an object, such as railway wheels, there are often used methods that do not destroy the object to be tested, so that this object may still be used according to its use. To allow such non-destructive testing, there are particularly used acoustic signals for such wear or remaining lifetime testing, because they have particularly good propagation properties in solids. An acoustic excitation signal is then applied to an object to be tested and a received impulse response to the excitation signal is stored digitally via sensors. From this received signal, i.e. the impulse response of the excitation signal, there is then performed a calculation of a short-time FFT in several time windows, which allows observation of the signal in the frequency domain. The result is represented in the form of a spectral representation (spectrogram). Therein, signal energy of the received impulse response signal is plotted as a function of time and frequency. This allows comprehensive characterization of the relevant oscillation modes and its attenuation behavior.

A precondition for an evaluation of the devices or objects to be tested is in most cases the performing of a training process in a preceding step. For this purpose, there is used a representative selection of good parts for the formation of a reference pattern.

The distance to the reference pattern is determined. Based thereon, a decision is made whether the device is good or faulty.

The introduction of a multi-class model allowed to manually define the classes created by this alteration as further good classes. When deviations from the training class occurred, the part or object was no longer defined as bad, instead there was the formation of a new class that was initially considered as undefined class and only by manual testing obtained the rating "good" and/or "bad".

For such a classification of the devices or objects, it has already been possible to successfully use the approach to classify structured, non-voice signals with methods of voice processing. In some cases, a simple DTW detector (DTW=dynamic time warping) may be used for this purpose, such as suggested, for example, in P. Holstein, M. Koch, D. Hirschfeld, R. Hoffmann, D. Bader, K. Augsburg: "A Strategy for Signal Recognition under Adverse Conditions" in: Proc. 32nd Conf. Internoise, 2003, Jeju Korea. In complicated cases, the concept of the hidden Markov models (HMM) is used, as it is exemplarily illustrated in FIG. 5. The application of such an HMM concept was, for example, suggested in the following documents: D. Zhang Y. Zeng, X. Zhou, Cheng Y: "The pattern recognition of non-destructive testing based on HMM", in: Proc. 4th World Congress on Intelligent Control and Automation (Cat. No. 02EX527), 2002, vol. 3, pp. 2198-2202, Piscataway, N. J., USA; P. Baruah and R. B. Chinnma: "HMMs for diagnostics and prognostics in machining processes," in: Proc. 57th Meeting of the Society for Machinery Failure Prevention Technology, 2003, pp. 389-398, Virginia Beach, USA; A. R. Taylor and S. R. Duncan: "A comparison of techniques for monitoring process faults," in: Proc. Conf. Control Systems, 2002, pp. 323-327, Stockholm, SE; H. Y. K. Lau: "A hidden markov model-based assembly contact recognition system," Mechatronics, vol. 13(8-9), pp. 1001-1023, 2003, ISSN 0957-4158.

Due to the well-defined sequential structure of a voice signal, hidden Markov models usually use simple left-right graphs, such as graph 500 in FIG. 5. These graphs consist of a set of so-called hidden nodes 1, . . . , 5 (also called states) connected to each other, and a function associating feature vectors with the states. Node 1 represents the input node of the hidden Markov model, and node 5 represents the output node of the hidden Markov model. The individual nodes 1 to 5 are connected to each other by connections 502 reflecting a transition probability from one node to a following node. The function associating feature vectors with the states is, in most cases, a mixture of Gauss distribution density functions in the feature space for each inner state of the HMM.

The limits of the conventional methods described above are, in most cases, that such methods react to slight production changes not affecting the quality of the device by sorting out good parts. Although the use of multi-class models is a first step in the solution of this problem, a relative large number of classes are generated in this way, which each time require the decision of the user whether the new class is a good or a bad class. The use of HMMs already achieves good results in simply structured signals. However, since signals occurring with more complicated problems of the non-destructive testing generally do not have simple structures like the left-right structure described above, such simple left-right structures cannot offer any determination of a quality class of the device to be tested or only a very imprecise determination.

Furthermore, the conference contribution, F. Wolfertstetter and G. Ruske: "Structured Markov models for speech recognition", in: Proc. ICASSP, 1995, pp. 544-547, Detroit, USA suggests an approach to use extended structure models for voice processing. These extended structure models in the form of stochastic Markov graphs allow improved synthesis and recognition of voice. However, this approach has proven to be disadvantageous because voice signals, as compared to the acoustic test signals mentioned above, are generated by completely different processes and thus also have different properties. A simple adoption of the special structure models in form of stochastic Markov graphs for non-destructive testing may thus not be done easily.

Also, in a conference contribution, M. Fichner, M. Wolff and R. Hoffmann: "A unified approach for speech synthesis and speech recognition using stochastic Markov graphs," in Proc. 6th Int. Conf. Spoken Language Processing (ICSLP), 2000, vol. 1, pp. 701-704, Beijing, PR China, and in the conference contribution, M. Eichner, S. Ohnewald, M. Wolff and R. Hoffmann: "Speech synthesis using Stochastic Markov Graphs," in: Proc. ICASSP, May 5-7, 2001, Salt Lake City, Utah, USA, there is suggested a possibility for voice recognition and/or voice synthesis on the basis of complex structure models in the form of stochastic Markov graphs. The above disadvantages and/or problems with the transfer of the complex structure models from voice processing to a non-destructive testing method apply here, too.

SUMMARY OF THE INVENTION

It is the object of the present invention to provide a more exact and less failure-prone way to perform a classification of a device to be tested into a quality class.

In accordance with a first aspect, the present invention provides a device for assessing a quality class of an object to be tested, having a unit for detecting an acoustic non-voice test signal from the object to be tested; a unit for providing a stochastic Markov model including states and transitions between states on the basis of reference measurements of objects of known quality classes, wherein, in the stochastic Markov model, a single probability density distribution is associated with each state, and wherein several states have transitions from a common predecessor state; a unit for evaluating the test signal using the stochastic Markov model; and a unit for associating the object to be tested with a quality class based on the evaluation of the test signal.

In accordance with a second aspect, the present invention provides a method for assessing a quality class of an object to be tested, having the steps of detecting an acoustic non-voice test signal from the object to be tested; providing a stochastic Markov model including states and transitions between states on the basis of reference measurements of objects of known quality classes, wherein, in the stochastic Markov model, a single probability density distribution is associated with each state, and wherein several states have transitions from a common predecessor state; evaluating the test signal using the stochastic Markov model; and associating the object to be tested with a quality class based on the evaluation of the test signal.

In accordance with a third aspect, the present invention provides a computer program with program code for performing the above-mentioned method when the program runs on a computer.

The present invention provides a device for assessing a quality class of an object to be tested, comprising: means for detecting a test signal from the object to be tested; means for providing a stochastic Markov model including states and transitions between states on the basis of reference measurements of objects of known quality classes; means for evaluating the test signal using the stochastic Markov model; and means for associating the object to be tested with a quality class based on the evaluation of the test signal.

Furthermore, the present invention provides a method for assessing a quality class of an object to be tested, comprising: detecting a test signal of the object to be tested; providing a stochastic Markov model including states and transitions between states on the basis of reference measurements of objects of known quality classes; evaluating the test signal using the stochastic Markov model; and associating the object to be tested with a quality class based on the evaluation of the test signal.

The present invention is based on the finding that complex structure models, such as the stochastic Markov model, may also be used for non-destructive testing methods, wherein in this case these stochastic Markov models have to include states and transitions between states formed on the basis of reference measurements of objects of known quality classes. Unlike voice processing and/or voice recognition, it is thus necessary when applying the stochastic Markov models to first correspondingly form the network structure of the stochastic Markov model, i.e. the transitions between individual states and the number and position of the states in the stochastic Markov model, using reference measurements of objects of known quality classes prior to the actual assessment of a quality class of an object to be tested. In voice processing, such forming of the transitions between individual states and the position of the individual states in the stochastic Markov model is often not necessary and, after the formation of the stochastic Markov model on the basis of a general psychoacoustic context, may then be used for an adjustment of accuracy during the classification of voice portions. The core idea of the present invention is thus that acoustic signals may also be used in non-destructive testing of objects and may be classified by methods such as the stochastic Markov models known from voice processing, wherein in this case, however, an appropriate formation of the states and transitions between the states must be taken care of The present invention has the advantage that the suggested approach is universally usable and completely data-controlled, and that only little knowledge of the underlying processes of the structuring of the test signal in the object to be tested is necessary. Compared to the current methods, particularly the use of HMM structures, in non-destructive testing, there are achieved clearly better, i.e. more precise results, which are additionally less failure-prone with respect to misclassification. For example, when using the stochastic Markov model, a significant improvement of the selectivity between the quality classes may be achieved as compared to the use of HMM structures. In that way, "good" devices may, for example, be distinguished from "bad" devices in nearly 100 percent of all cases. When determining a lifetime of the object to be tested using the stochastic Markov models, an aging state of the object to be tested may be recognized correctly in approximately 98% of all cases. It is thus a significant advantage of the present invention that the structure models of the stochastic Markov models known from voice processing and/or voice recognition may also be used for non-voice applications, such as non-destructive testing, after adaptation, and thus the advantages of the use of stochastic Markov models in the form of a more precise classification possibility are also usable for the non-voice applications.

The core of the invention is thus the application of stochastic Markov models or graphs for the classification of non-voice acoustic signals. There is performed automatic "structure exposition" of the signals and modeling as stochastic Markov graphs or models.

BRIEF DESCRIPTION OF THE DRAWINGS

Preferred embodiments of the present invention will be explained in the following in more detail with reference to the accompanying drawings, in which.

DESCRIPTION OF THE PREFERRED EMBODIMENTS

Figure 1:
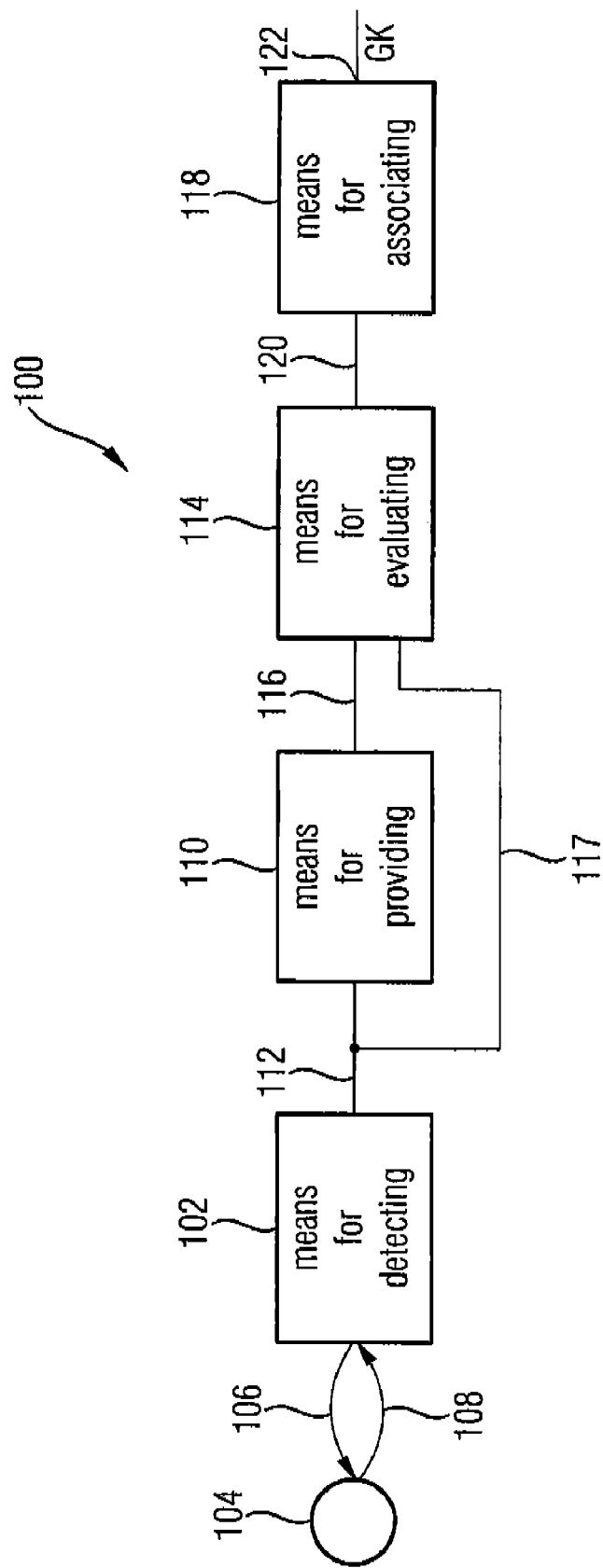
FIG. 1 shows a block circuit diagram of an embodiment of the present invention.

In the following description of the embodiments of the present invention, the same or similar reference numerals are used for the elements illustrated in the various drawings and operating in a similar way, wherein a repeated description of these elements is omitted.

FIG. 1 shows a block circuit diagram of an embodiment of the present invention. The device 100 for assessing a quality class of an object to be tested includes means 102 for detecting a (for example acoustic) test signal 108 from the object 104 to be tested or for applying an acoustic excitation signal 106 to the object 104 to be tested to detect a test signal 108 based thereon. Furthermore, the device 100 for assessing includes means 110 for providing a stochastic Markov model. The means 110 for providing is connected to the means 102 for detecting via a connection 112. Furthermore, the device 100 for assessing includes means 114 for evaluating the test signal using the stochastic Markov model, wherein the means 114 for evaluating is connected to the means 110 for providing via a second connection 116 and to the means 102 for applying via a further connection 117. Furthermore, the device 100 for assessing includes means 118 for associating the object 104 to be tested with a quality class GK based on the evaluation of the test signal 108. The means 118 for associating is further connected to the means 114 for evaluating via a third connection 120 and further comprises an output 122 at which a signal may be tapped off that allows conclusions as to the quality class GK with which the means 118 for associating has associated the object 104 to be tested.

In order to test an object 104 to be tested with respect to certain parameters, such as manufacturing quality, wear or operating state, the means 102 for detecting may supply an acoustic excitation signal 106 to the object 104 to be tested, wherein the acoustic excitation signal 106 is, for example, an ultrasonic impulse or the like applied to the object 104 to be tested via a solid (or liquid and/or gaseous) connection (active detection). In response to the acoustic excitation signal 106, a characteristic acoustic pattern, which may be detected as test signal 108, may form in the object 104 to be tested corresponding to a characteristic structure to be tested in the object 104, for example corresponding to material erosion in a wear examination.

Alternatively, the test signal 108 may also be determined by passive detection, wherein in that case the application of the excitation signal 106 to the object 104 to be tested may be omitted, wherein a signal emitted by the object to be tested may be used.

This test signal 108 may then, for example, be transmitted to the means 102 for detecting again using a solid, liquid or gaseous (for example air) connection and correspondingly processed therein. This processing may, for example, be a time spectral analysis using a Fourier or wavelet transform, whereby the test signal 108 in the form of a three-dimensional time-frequency representation reflects the amplitudes at the respective points in time and frequency. Furthermore, in the means 102 for detecting, there may already be done an extraction of the features (i.e. the amplitudes) into an n-th dimension feature space and subsequently a transformation of the n-th order feature space may be transformed to an m-th dimension feature space, wherein n and m are natural numbers satisfying the condition m>n. Such a transformation thus offers the possibility not to use all possible feature instances (for example all obtained amplitude values of the time-frequency domain representation) for assessing the object to be tested, but to use only those feature instances that include a specific information on the characteristic pattern in the test signal 108. Such a reduction of the dimension of the feature space then also results in a simplification of the subsequent steps, because a smaller number of feature instances has to be taken into account. The feature instances of the test signal 108 detected (and possibly transformed) by the means 102 for detecting may then be grouped and/or subdivided into feature vectors $\underline{X}$.

The formed feature vectors may then be transmitted to the means for providing the stochastic Markov model via the connection 112. In a first version, the means 110 for providing the stochastic Markov model may include an already trained stochastic Markov model, if the device 110 is to serve only for the classification of objects 104 to be tested into known quality classes and training for new quality classes is not required. For example, such a fixedly trained device would be conceivable in the form of a testing installation for the wear of railway wheels, wherein such a testing installation could be installed in each repair workshop for railway vehicles; however, the thresholds of wheel wear may be given, for example, by the national railway authorities, and thus a new classification into the quality classes "okay" or "not okay" does not have to be newly set by somebody working in the repair workshop.

On the other hand, the means 110 for providing the stochastic Markov model may also be designed to be able to perform training for a new quality class, wherein such a device 110 for assessing a quality class of an object to be tested may in that case, for example, be installed in research or production installations, wherein readjustment of the quality classes may become necessary if production process changes in the production of the object to be tested result in a misclassification into the existing quality classes or result in the generation of a large number of new undefined quality classes.

In one of the following paragraphs, there will be a more detailed discussion of the description of the differences of the use of conventional HMM graphs and SMM graphs (SMM=stochastic Markov model, also referred to as SMG) and corresponding training.

Furthermore, the feature vectors formed in the means 102 for detecting may then be transmitted to the means 114 for evaluating in the form of a feature vector sequence $\underline{X}$ via the further connection 117, wherein the means 114 for evaluating also receives the same via the second connection 116 from the means 110 for providing the stochastic Markov model. Based on the feature vectors $\underline{X}$ supplied via the further connection 117 and the stochastic Markov model supplied via the second connection 116, the means 114 for evaluating may determine a classification signal in a process explained in more detail below, the signal being communicated to the means 118 for associating the object to be tested with a quality class GK via the connection 120. From this classification signal, the means 118 for associating may then perform an association of the object 104 to be tested with a quality class GK, for example using a decision threshold, wherein information on the quality class GK with which the object 104 to be tested was associated may be picked up at the output 122 of the means 118 for associating.

Figure 2:
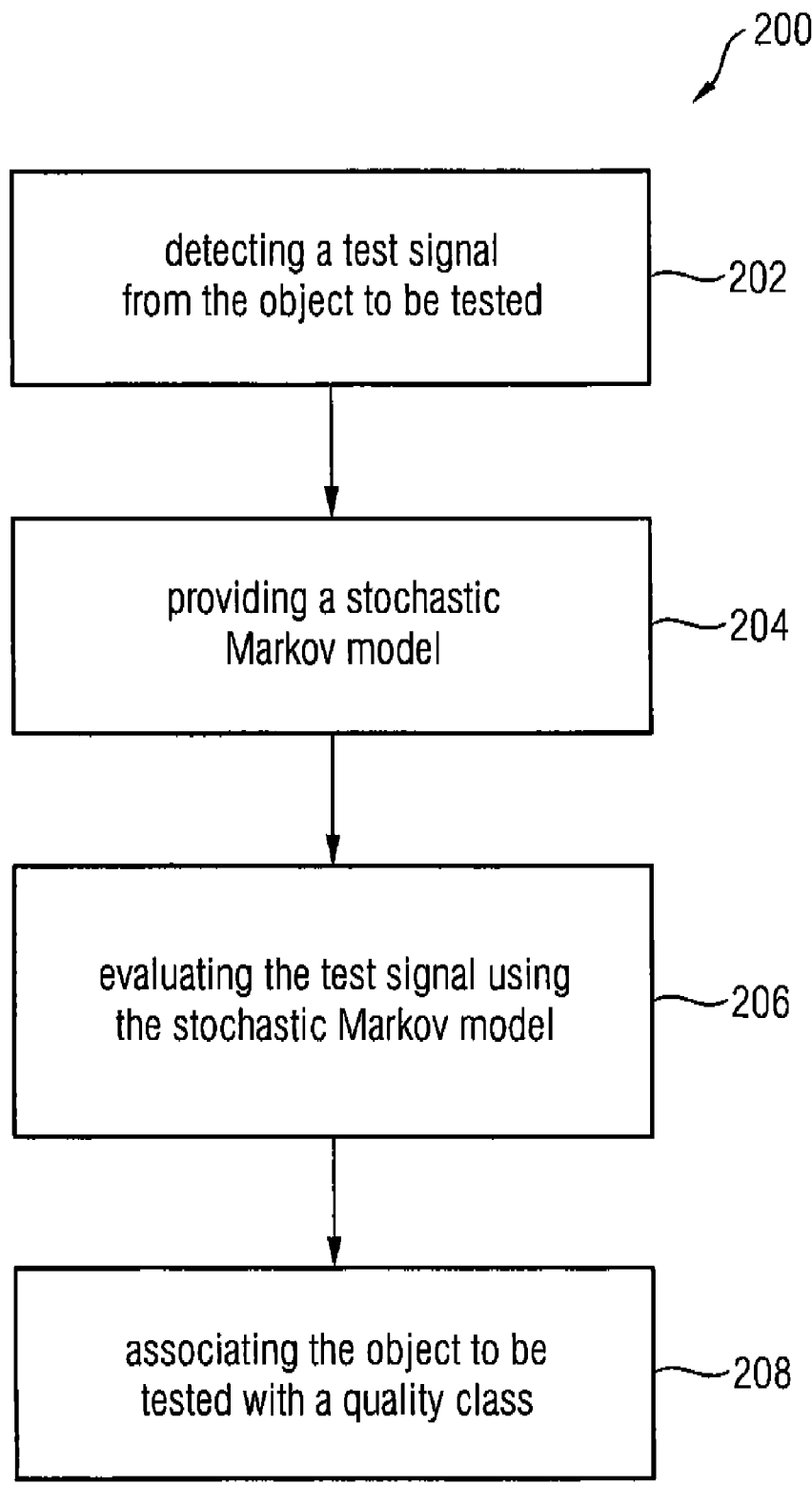
FIG. 2 shows a block circuit diagram of a first embodiment of the inventive method.

FIG. 2 shows a first embodiment of the inventive method, wherein the method 200 illustrated in FIG. 2 essentially shows the sequence of method steps as already explained in more detail with reference to FIG. 1. In a first step 202, there is a detection of a test signal from the object to be tested (passive detection) or an application of an acoustic excitation signal to the object to be tested, wherein the application then further includes detecting the test signal based on the acoustic excitation signal (active detection). Furthermore, the step of applying 202 may also include a time/frequency domain transformation of the detected test signal to combine amplitudes of the time and frequency domains as features x in a feature vector $\underline{X}$ and to form a feature vector sequence $\underline{X}$ of several feature vectors $\underline{X}$. In addition, it is possible to perform a feature transformation to perform data reduction with respect to the decisive features of the test signal to facilitate subsequent processing of the feature vectors.

In a further method step 204, a stochastic Markov model may be provided, wherein the stochastic Markov model is either already pre-trained or may be trained on the basis of the feature vectors formed in the method step 202 of detecting, wherein in that case the feature vectors are to be related to objects with known quality classes during training (formation of reference feature vectors).

In a further method step 206, there is an evaluation of the test signal using the stochastic Markov model to obtain a classification signal with the help of which an association of the object to be tested with a quality class may be performed in a further method step 208.

The basic elements of the approach may thus be distinguished by the four essential steps of feature extraction and feature transformation, provision (and possibly training) of the stochastic Markov model, classification of features and association of the classified features with a quality class.

The essential feature of the present invention is the use of an acoustic model structured as stochastic Markov graph (SMG) and representing a generalized form of HMMs. Unlike HMMs, the graph structure of the used stochastic Markov model is, however, significantly more complicated and should be implemented in a special way for the use of the stochastic Markov graph in acoustic non-destructive test methods. This may be done, for example, in a special training of the stochastic Markov graph, whereupon the trained stochastic Markov graph may be used for the classification of an object to be tested.

A stochastic Markov graph may be represented by the formula $$G=\{V, E, \{N\}, v^{(V)}, \pi^{(E)}\},$$

wherein the stochastic Markov graph G consists of a set of nodes (or states) V and a set of directional edges $E \subseteq V \times V$. By the mapping $v^{(V)}: V \rightarrow \{N\}$, a multidimensional Gauss distribution density function $N_i(\mu_i, \Sigma_i) \in \{N\}$ is associated with each node, the function being defined as a certain area in the secondary feature space, i.e. in the feature space with the second (smaller) dimension. As in conventional HMMs, each edge has a transition probability $\pi^{(E)}: E \rightarrow \Re^{(0,1]}$, wherein $\Re^{(0,1]}$ indicates the set of real numbers r with $0 < r \leq 1$.

For the first basic step of feature extraction and transformation of the acoustic signals (i.e. the test signal), there is, for example, used a feature extraction based on short-time FFT. The features of the acoustic signal (i.e. the test signal) may, for example, be the amplitudes at corresponding points in frequency and time of the short-time FFT. As a robust estimation of the Gauss distributions with the given feature space $\underline{X}$ opened up by the features x recognized in the feature extraction would require a very large amount of training data, the dimension of the feature space should be reduced. This may be done by a secondary feature transformation using a main component analysis (PCA=HKA). Such a main component analysis reduces primary feature vectors generated by features x from the feature extraction to secondary feature vectors, wherein the features of the secondary feature vectors or information on the features of secondary feature vectors only include features or information relevant for an assessment of the quality class of the object to be tested. This allows to perform a significant reduction of the dimension of a primary feature vector space with the primary feature vectors to a secondary feature space of the secondary feature vectors, which is characterized in a significant simplification of the downstream numerical effort.

As subsequent significant part of the inventive approach, there is then performed providing and/or training of the stochastic Markov graph. In particular, training of the stochastic Markov graph is to be discussed in more detail in this context. The training of the stochastic Markov graphs firstly includes the determination of acoustic parameters, such as the mean value vector $\mu_i$ and the covariance matrix $\Sigma_i$ of the Gauss distributions $N_i$. The index i characterizes a state (i.e. node) of the stochastic Markov graph. Secondly, the training includes the determination of the graph structure $\{V, E, \pi^{(E)}\}$ of the stochastic Markov graph. The training method described here executes these two tasks at the same time, as will be explained in more detail below.

Figure 3:
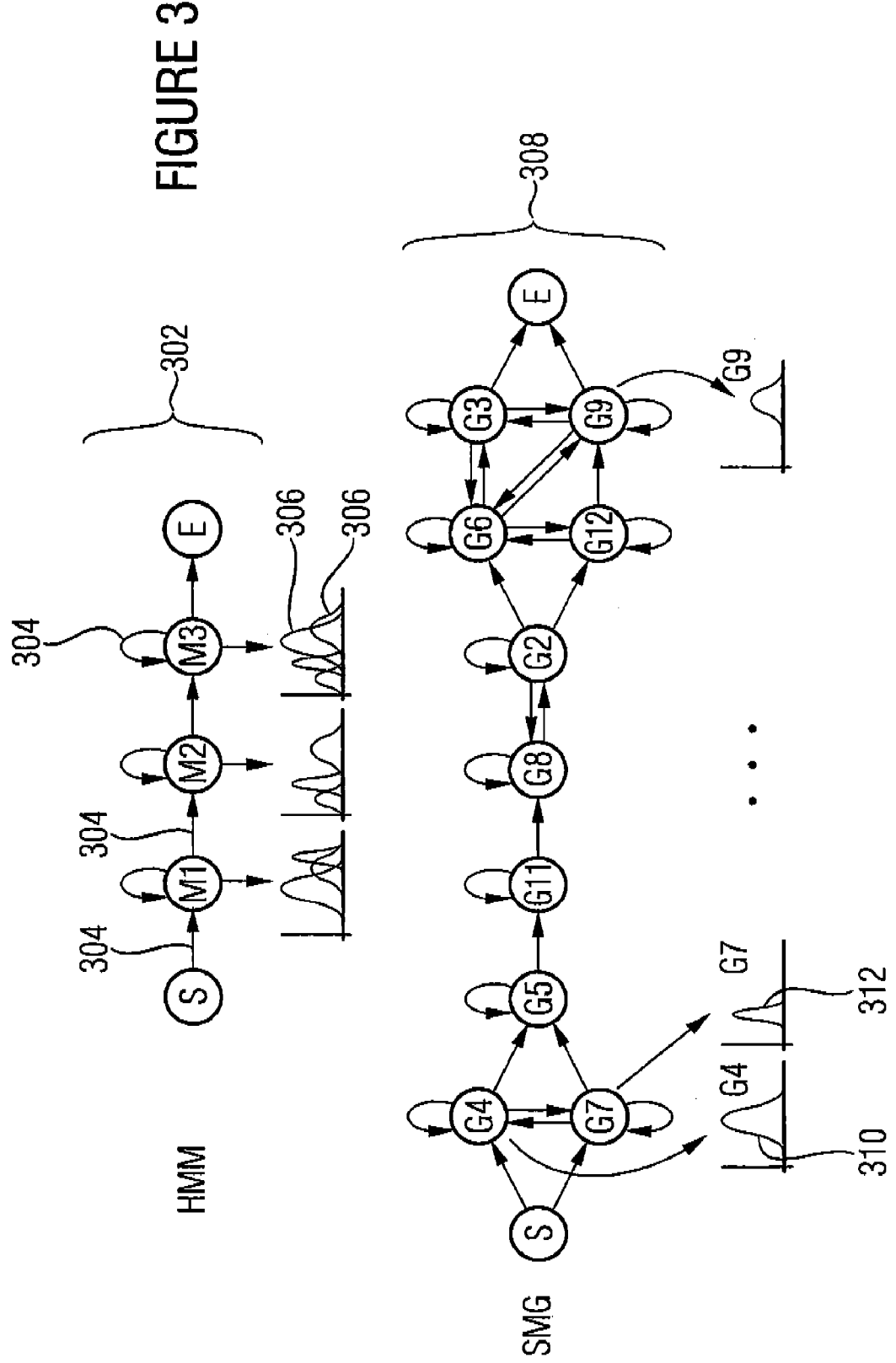
FIG. 3 is a schematic representation of a network structure of an HMM graph and an SMM graph for illustrating the differences between HMM graphs and SMM graphs.

In a first step of the training, an SMG model (SMG=stochastic Markov graph) is generated for each observation class (i.e. quality class). These models are initialized by an equivalent generation of a left-right HMM structure with M nodes, the association of the Gauss distributions with the nodes and the initialization of the parameters with a sufficiently large amount of feature vectors of the observation. All models are subsequently trained in an equivalent manner. Such a left-right HMM structure is again illustrated in FIG. 3 and indicated by the reference numeral 302. This left-right HMM structure 302 includes three nodes S, M1, M2, M3 and E, which are connected to each other by directional edges, wherein some of the directional edges in FIG. 3 are exemplarily indicated by the reference numeral 304. One (or more) normal distribution(s) or Gauss distribution(s) are associated with each of the inner nodes M1 to M3, as illustrated exemplarily in FIG. 3 by the reference numerals 306. First, there is then an iterative refinement of the parameters of the Gauss distributions by, for example, applying the Viterbi algorithm. Furthermore, the transition probability between the nodes of the SMGs is determined. After the Viterbi training (a training on the basis of the Viterbi algorithm) is converged, there is some tidying of the SMGs by erasing all edges whose transition probabilities are below a given transition probability threshold. After that, splitting of all Gauss distributions (and their corresponding SMG nodes) is performed along the axis of their largest standard deviations. The new nodes (i.e. both nodes resulting from the division) have the transitions to all predecessors and successors of the original nodes. The process of the Viterbi training, the tidying and the splitting is repeated until either a predetermined number of SMG nodes has been reached or a predetermined number of nodes has been erased during tidying. The model should not be overtrained, i.e. if a training portion does no longer cause an improvement larger than a predetermined improvement threshold, the training of the stochastic Markov graph may be cancelled. After the training, particularly the splitting of the individual nodes M1 to M3 and the tidying of nodes and transitions between nodes having a lower transition probability than the transition probability threshold, the result is, for example, a stochastic Markov graph with 10 states (nodes) S, G4, G7, G5, G11, G8, G2, G12, G6, G9, G3 and E, as indicated by the reference numeral 308 in FIG. 3. The transition probabilities of the transitions between the nodes of the SMG 308 are not illustrated for reasons of clarity. As can be seen from FIG. 3, the splitting of the nodes of the graph allows to associate a single normal or Gauss distribution with each node, as illustrated, for example, by the association of the probability density 310 with node G4, of the probability density 312 with node G7 or of the probability density 314 with node G9. Although this increases the complexity of the graph, the classification quality increases as well when using this graph.

After such a trained stochastic Markov graph SMG 308 has been provided, the evaluation of the test signal using the provided (and trained) stochastic Markov graph and the association of the object to be tested with a quality class may be performed. For this purpose, there is first formed a linear graph X from a feature vector sequence $\underline{X}$ of the observation for decoding (i.e. an evaluation of the test signal for a classification), wherein the feature vector sequence $\underline{X}$ is composed of the individual feature vectors $X_1, X_2, X_3 \ldots$ etc., and the individual feature vectors correspond, for example, to amplitude values at points in time and frequency of a portion from the time-frequency domain representation. Furthermore, the linear graph X associates exactly one feature vector with a node of the graph. Afterwards, there is an adaptation of the graph to the SMG models $G_m$ of all M observation classes. As local distance measure between the feature vector $X_j$ (wherein the index j indicates a node $v_j$) and a Gauss distribution of the node $v_j$ of the m-th SMG model $G_m$, the log-likelihood LL (credibility) is used, which characterizes an emission probability of the feature instances $x_i$ of a feature vector $X_i$ and may be described by the following formula:

$$LL(x_i \mid N(v_{j,m})) = -(x_i - \underline{\mu}_{j,m})^T \cdot \sum_{j,m}^{-1} (x_i - \underline{\mu}_{j,m}) - \ln \left| \sum_{j,m} \right|$$

Here, the term $N(v_{j,m}) = (\underline{\mu}_{j,m}, \Sigma_{j,m})$ denotes the Gauss distribution connected to the node $v_j$ of the SMG m, wherein the term $\underline{\mu}_{j,m}$ denotes the mean value vector of the j-th node of the m-th SMG model, and the term $\Sigma_{j,m}$ denotes the covariance matrix of the j-th node of the m-th SMG. A Viterbi search determines a path $U^*_m$ through the stochastic Markov graph $G_m$ maximizing the emission probability sum for the feature vector sequence $\underline{X}$ of the observation, which may be expressed mathematically by the following formula:

$$U^*_m = \underset{U \subseteq G_m \times \underline{X}}{\mathrm{argmax}} \left[ \sum_{i=1}^{|X|} LL(\underline{x}_i \mid N(u_i)) \right]$$

$N(u_i)$ denotes a Gauss distribution connected to the node $u_i \in U$, and $|\underline{X}|$ denotes the length of the feature vector sequence $\underline{X}$. The term $LL^*(\underline{X} \mid G_m)$ may further denote the emission probability of the best path in the model $G_m$ with given feature vector sequence $\underline{X}$.

In the case of a multi-class model (M>1), the model m* is selected that provides the largest emission probability for the observation as recognition result, which may be expressed by the following formula:

$$m^* = \underset{G_m}{\mathrm{argmax}}\, LL^*(\underline{X} \mid G_m)$$

Furthermore, the emission probability m* and/or $U^*_m$ may be used as confidence measure, which allows to make a statement as to how similar observation and selected class are.

Figure 4:
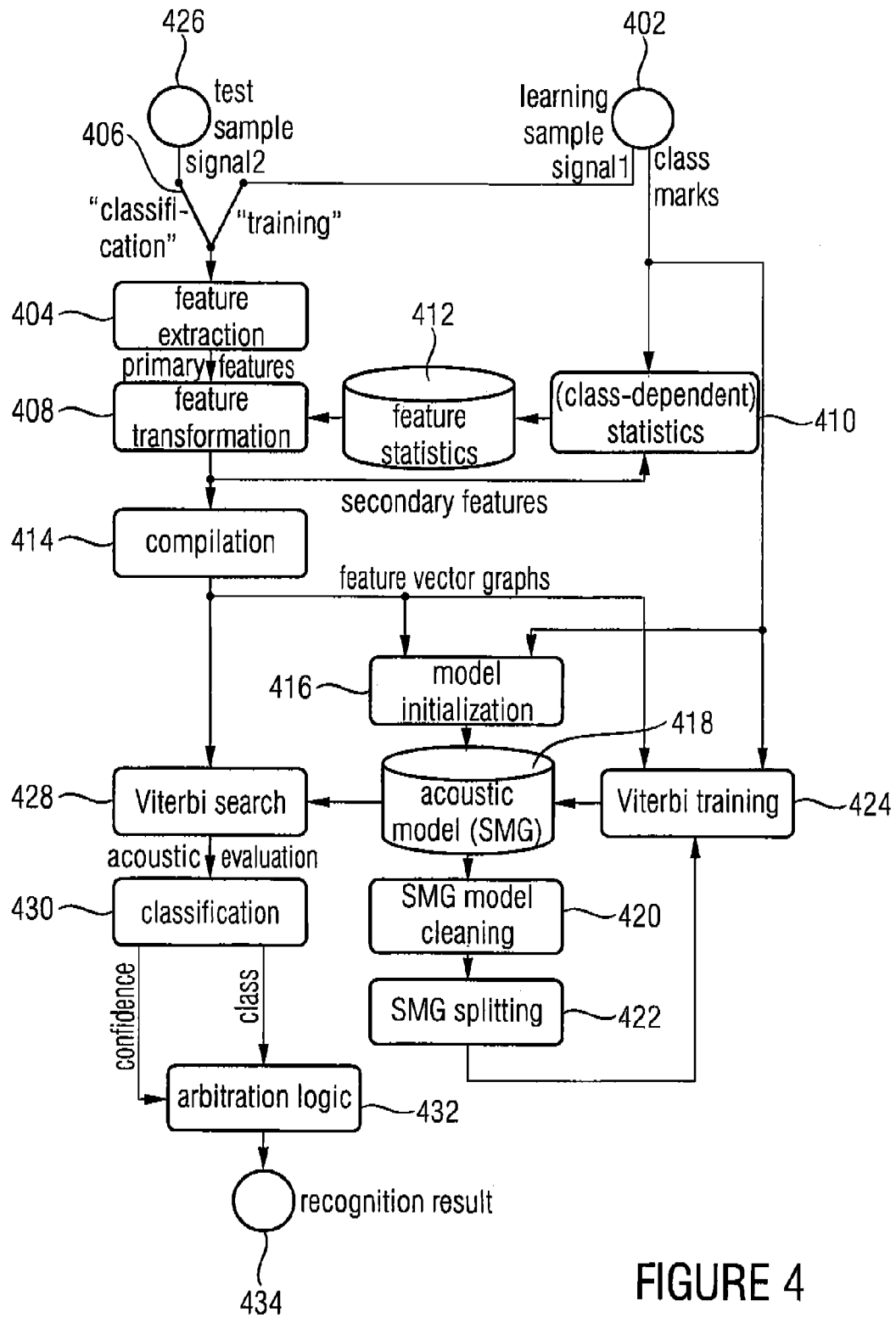
FIG. 4 shows a second embodiment of the inventive method.
Figure 5:
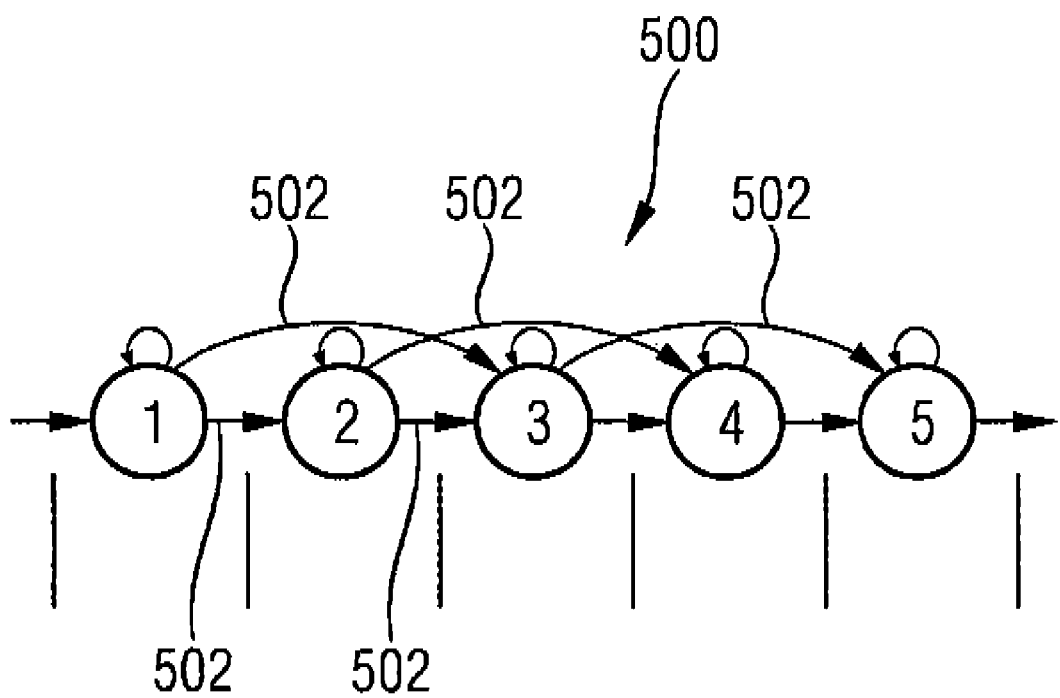
FIG. 5 is a representation of a network topology of an HMM graph, as used in conventional approaches.

FIG. 4 shows a flow diagram of a second embodiment of the inventive method, in which a training of the stochastic Markov graph is performed. First, a signal1 is provided to feature extraction stage 404 by a learning sample 402, wherein a switch 406 is switched in the position "training" illustrated in a dashed line in FIG. 4. The feature extraction stage 404 determines primary features and, in a feature transformation stage 408, these primary features are further transformed to secondary features. The secondary features are supplied to a statistical unit 410 for class-dependent processing, wherein the statistical unit 410 simultaneously contains information on the class marks inherent to signal1 from the learning sample 402. The statistical unit 410 may then determine characteristic feature statistics, as indicated by reference numeral 412 in FIG. 4. These feature statistics 412 then include information on significant feature instances of signal1, from which result conclusions with respect to the class of the test object associated with signal1. In particular, this means that a relationship may be determined in the feature statistics 412 allowing a recognition of the class on the basis of few relevant features, whereby a reduction of the features important for an unambiguous classification becomes possible in the feature transformation 408. The feature statistics 412 may thus serve as basis for the feature transformation 408, which is indicated in FIG. 4 by the connection between the elements with the reference numerals 412 and 408. Furthermore, the secondary features may be converted to feature vector graphs by a compilation 414, wherein the graphs may first be used for model formation as model initialization 416. Furthermore, the information on the class marks provided by the learning sample 402 may also be taken into account in the model initialization 416. From the model initialization, an acoustic model 418 may be provided in the form of a stochastic Markov graph (SMG), which may be changed within the model training by the steps of SMG model cleaning 420 and SMG splitting 422 as well as the subsequent Viterbi training 424. The Viterbi training 424 may use information from the SMG splitting 422, the information on class marks output by the learning sample 402 and the feature vector graph provided after the compilation 414 to change various states and transitions between various states of the acoustic model. Such a training may be done over several cycles of SMG model cleaning 420, SMG splitting 422 and Viterbi training 424, wherein the acoustic model 418 is to be considered as sufficiently trained when a further training loop does not yield any significant change of the model structure. Such a training termination may, for example, occur after a threshold has been given and a quantity determined in the training process has been compared to the threshold. When the acoustic model 418 is sufficiently trained, the switch 406 may be switched from the position "training" to the position "classification", and unknown data of a test sample 426 of objects whose quality class is not known may be supplied to the feature extraction 404. This is done via signal2, which is, for example, a time domain signal, which is subjected to a short-time FFT in the feature extraction 404, wherein the primary features in this case are, for example, amplitudes at defined points in time and frequency. The primary features are then converted to secondary features by the feature transformation 408, which are then again converted to a feature vector graph by a compilation 414. The feature vector graph is then supplied to a Viterbi search 428, which performs an acoustic evaluation of the feature vector graph considering the acoustic model 418 and provides information in a subsequent classification 430 allowing a direct association of the test object from which signal 2 comes. The classification in the unit indicated by reference numeral 430 may thus firstly provide a signal CLASS, from which an arbitration logic 432 provides a recognition result 434 (i.e. an association of the object to be tested with a quality class), for example using a decision threshold. However, the arbitration logic 432 does not have to operate on the basis of a decision threshold, instead there may be used problem-dependent decision criteria to be set according to the desired test task with non-voice acoustic signals. Furthermore, "CONFIDENCE" information may be provided to the arbitration logic 432 by the classification 430, from which the arbitration logic would make a statement on a possible deviation of the decision result from a "true classification result" using the acoustic model 418. Such a confidence measure may, for example, be a deviation between a value of the signal CLASS (for example the value $U^*_m$) and a characteristic value, for example a mean value of values of the signal CLASS associated with the quality class. Such "CONFIDENCE" information and/or such a confidence measure thus also allow a statement on the quality of the association of an object to be tested with a quality class.

Depending on the circumstances, the inventive method for assessing a quality class of an object to be tested may be implemented in hardware or in software. The implementation may be done on a digital storage medium, particularly a floppy disc or CD with control signals that may be read out electronically, which may cooperate with a programmable computer system so that the corresponding method is executed. In general, the invention thus also consists in a computer program product with a program code stored on a machine-readable carrier for performing the inventive method when the computer program product runs on a computer. In other words, the invention may thus be realized as a computer program with a program code for performing the method when the computer program runs on a computer.

Summarizing, non-voice acoustic signals may be analyzed and classified by the above method and the above device, wherein algorithms of voice processing, particularly the structure models of the stochastic Markov graphs, may be used to develop a universal method not refined for a particular test task. In contrast to the procedures known from voice processing, special adaptation of the used structure models is necessary in this case of application. The method described in the above discussion may particularly be used for the following technical fields of application:

Production monitoring ("process integrated non-destructive testing"—PINT)

The properties of production processes (or those of devices flowing from the production process) may be monitored and evaluated. The developed algorithm should automatically react to production changes not affecting the quality of the produced device and adapt itself thereto.

Lifetime analysis ("life cycle prediction")

Mostly, smaller devices (valve seats, contact areas of contactors), but also, for example, railway wheels, are examined with respect to wear in the intended use. In addition to the wear examinations, a representative prediction of the remaining lifetime is performed to prevent impending failure in time.

State monitoring ("health monitoring")

Here, structural safety and guaranteeing operational strength are most important. Thresholds are determined and evaluated. An example is the state monitoring of construction elements in airplanes. For example, the integrity of airplane hull shells may be permanently monitored during the flight.

In contrast to voice recognition, the present invention is based on a special adaptation and application of the method of voice recognition to technical signals. However, a simple adaptation of the method cannot work for the following reasons:

In the present invention, the signals to be classified (test signals) are generated by completely different processes and thus also have different properties according to which classification may be done.

The feature extraction for voice is psychoacoustically motivated (mel-scaled bands). The features for technical signals may be completely different, and thus a simple transfer of voice data recognition to the recognition of structures in technical signals may not be employed directly, but only with suitable adaptations.

For technical signals, the model structure is not known in most cases. Thus structure training is necessary, which is not necessarily required in voice recognition. Instead, a basic structure modulation may already be done for voice signals with the help of known psychoacoustic background, which, in most cases, provides useful results even in a hardly trained (or untrained) state.

The classification strategy for technical signals is different from that for voice recognition. For the classification of technical signals, there are considered, among other things, decision thresholds or the behavior of confidence information. In voice recognition, the classification task consists in an output of symbol sequences and/or sets.

While this invention has been described in terms of several preferred embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

What is claimed is:

1. A device for assessing a quality class of a device under test, comprising:
   a unit for detecting an acoustic non-voice test signal from the device under test;
   a unit for providing a stochastic Markov model including states and transitions between states on the basis of reference measurements of devices of known quality classes, wherein, in the stochastic Markov model, a single probability density distribution is associated with each state, and wherein several states have transitions from a common predecessor state;
   a unit for evaluating the acoustic non-voice test signal using the stochastic Markov model; and
   a unit for associating the device under test with a quality class based on the stochastic Markov model evaluation of the acoustic non-voice test signal.

2. The device for assessing according to claim 1, further comprising a unit for applying an acoustic excitation signal to the device under test, wherein the unit for detecting is designed to detect the test signal in response to the acoustic excitation signal.

3. The device for assessing according to claim 1, wherein the unit for providing is designed to receive reference measurement data of devices of known quality classes to form states and transitions between the states in the stochastic Markov model based on the reference measurement data.

4. The device for assessing according to claim 3, wherein the unit for providing is designed to associate one transition probability each with the transitions between the states, wherein the unit for providing is further designed to prevent a transition between a first state and a second state if the transition probability from the first state to the second state is less than a predetermined threshold.

5. The device for assessing according to claim 3, wherein the unit for providing is designed to split a state into a plurality of states.

6. The device for assessing according to claim 1, wherein the unit for detecting is designed to extract, when detecting the test signal, the same into a primary n-th dimension feature space and to transform the primary n-th dimension feature space to a secondary m-th dimension feature space, wherein m and n are natural numbers meeting the condition that m is larger than n.

7. The device for assessing according to claim 1, wherein the unit for providing is designed to assign a probability density function and a feature vector formed from signal values of the test signal to each state of the stochastic Markov model.

8. The device for assessing according to claim 7, wherein the unit for evaluating is designed to form a log-likelihood between the probability density function of the state and the feature vector assigned to the state.

9. The device for assessing according to claim 7, wherein the unit for evaluating is designed to perform the stochastic Markov model evaluation on the basis of the Viterbi algorithm.

10. The device for assessing according to claim 1, wherein the unit for evaluating is designed to output a classification value for determining a quality class, and the unit for associating is designed to use the classification value for associating the device under test with the quality class, wherein the unit for associating is further designed to use a deviation between the classification value and a value characteristic for the quality class as confidence measure for a similarity of the device under test with respect to a quality class.

11. The device for assessing according to claim 1, wherein the unit for providing is designed to provide a first Markov model associated with a first quality class and to provide a second stochastic Markov model associated with a second quality class including second states and second transitions between the second states on the basis of reference measurements of devices of known quality classes, wherein the unit for evaluating the test signal is designed to use the second stochastic Markov model for an evaluation of the test signal into the first quality class or the second quality class.

12. The device for assessing according to claim 1, wherein the unit for associating is designed to perform the association of the device under test with the quality class on the basis of a decision threshold.

13. The device for assessing according to claim 1, wherein the acoustic non-voice test signal comprises an ultrasonic signal.

14. The device for assessing according to claim 1, wherein the known quality classes include good and bad.

15. The device for assessing according to claim 1, wherein the unit for providing is configured to generate a stochastic Markov graph for each quality class in an automatic manner based on reference measurement data of devices of known quality classes, wherein generating the stochastic Markov graph comprises changing the number and arrangement of states and transitions thereof during a training phase.

16. A method for assessing a quality class of a device under test, comprising:
    detecting an acoustic non-voice test signal from the device under test;
    providing a stochastic Markov model including states and transitions between states on the basis of reference measurements of devices of known quality classes, wherein, in the stochastic Markov model, a single probability density distribution is associated with each state, and wherein several states have transitions from a common predecessor state;
    evaluating the acoustic non-voice test signal using the stochastic Markov model; and
    associating the device under test with a quality class based on the stochastic Markov model evaluation of the acoustic non-voice test signal.

17. The method according to claim 16, wherein the acoustic non-voice test signal comprises an ultrasonic signal.

18. The method according to claim 16, wherein the known quality classes include good and bad.

19. The method for assessing according to claim 16, wherein providing a stochastic Markov model comprises generating a stochastic Markov graph for each quality class in an automatic manner based on reference measurement data of devices of known quality classes, wherein generating the stochastic Markov graph comprises changing the number and arrangement of states and transitions thereof during a training phase.

20. A non-transitory computer readable medium encoded with a computer program for assessing a quality class of a device under test , when the program runs on a computer, comprising: detecting an acoustic non-voice test signal from the device under test; providing a stochastic Markov model including states and transitions between states on the basis of reference measurements of devices of known quality classes, wherein, in the stochastic Markov model, a single probability density distribution is associated with each state, and wherein several states have transitions from a common predecessor state; evaluating the acoustic non-voice test signal using the stochastic Markov model; and associating the device under test with a quality class based on the stochastic Markov model evaluation of the acoustic non-voice test signal.

21. The computer readable medium according to claim 20, wherein the acoustic non-voice test signal comprises an ultrasonic signal.

22. The computer readable medium according to claim 20, wherein the known quality classes include good and bad.

23. The computer readable medium according to claim 20, wherein providing a stochastic Markov model comprises generating a stochastic Markov graph for each quality class in an automatic manner based on reference measurement data of devices of known quality classes, wherein generating the stochastic Markov graph comprises changing the number and arrangement of states and transitions thereof during a training phase.

* * * * *